United States Patent [19]

Geremia et al.

[11] Patent Number: 5,108,407
[45] Date of Patent: Apr. 28, 1992

[54] METHOD AND APPARATUS FOR PLACEMENT OF AN EMBOLIC COIL

[75] Inventors: Glen K. Geremia, Oaklawn; Michael Haklin, Palos Hills, both of Ill.

[73] Assignee: Rush-Presbyterian St. Luke's Medical Center, Chicago, Ill.

[21] Appl. No.: 535,386

[22] Filed: Jun. 8, 1990

[51] Int. Cl.⁵ ............... A61F 2/00; A61B 17/00; A61M 5/00
[52] U.S. Cl. .................. 606/108; 604/57; 606/1; 606/27; 623/1; 623/12; 623/900
[58] Field of Search ............ 604/8, 27, 28, 57, 96; 128/898; 606/28, 78, 108, 191, 194, 195, 198, 200, 1; 623/1, 12, 900

[56] References Cited

U.S. PATENT DOCUMENTS

| | | | |
|---|---|---|---|
| 3,868,956 | 3/1975 | Alfidi et al. | 606/78 |
| 4,503,569 | 3/1985 | Dotter | 604/8 |
| 4,512,338 | 4/1985 | Balko et al. | 606/78 |
| 4,735,201 | 4/1988 | O'Reilly | 606/28 |
| 4,795,458 | 1/1989 | Regan | 606/194 |
| 4,856,516 | 8/1989 | Hillstead | 606/1 |
| 4,994,066 | 2/1991 | Voss | 606/108 |
| 5,019,085 | 5/1991 | Millstead | 606/108 |
| 5,026,377 | 6/1991 | Burton et al. | 606/108 |
| 5,037,427 | 8/1991 | Harada et al. | 606/108 |
| 5,042,980 | 8/1991 | Baker et al. | 606/194 |
| 5,059,211 | 10/1991 | Stack et al. | 606/108 |

Primary Examiner—Stephen C. Pellegrino
Assistant Examiner—Glenn K. Dawson
Attorney, Agent, or Firm—Fitch, Even, Tabin & Flannery

[57] ABSTRACT

Method and apparatus for placing therapeutic devices such as embolic coils includes a probe assembly carried within a catheter. The probe assembly includes a fiber-optic cable with a connector retained thereon by crimping. The connector has a cable-receiving end resembling a ferrule, which is crimped about the cable. The other end of the connector provides mounting of a therapeutic device, such as an embolic coil. Heat releasable adhesive bonds the therapeutic device to the mounting portion of the connector. Laser energy transmitted through the fiber-optic cable is converted to heat by the connector, which thereupon becomes heated, releasing the adhesive bond between the connector and the therapeutic device. The probe assembly can then be withdrawn from the treatment site.

13 Claims, 2 Drawing Sheets

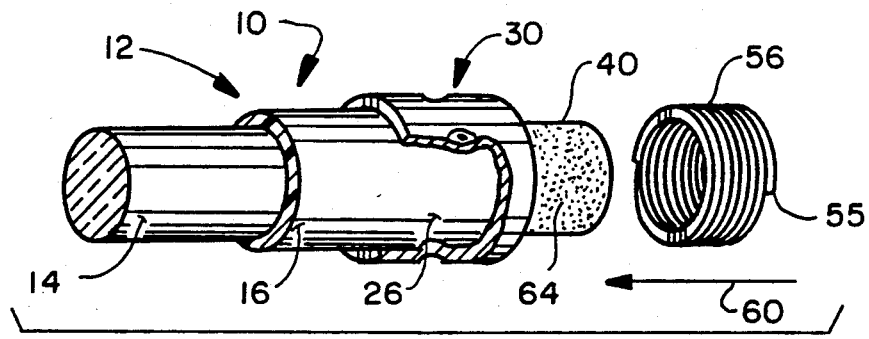
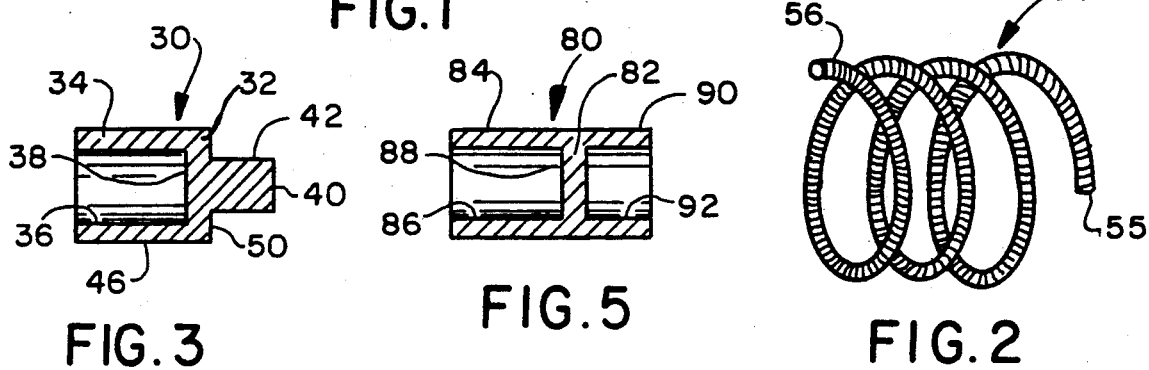
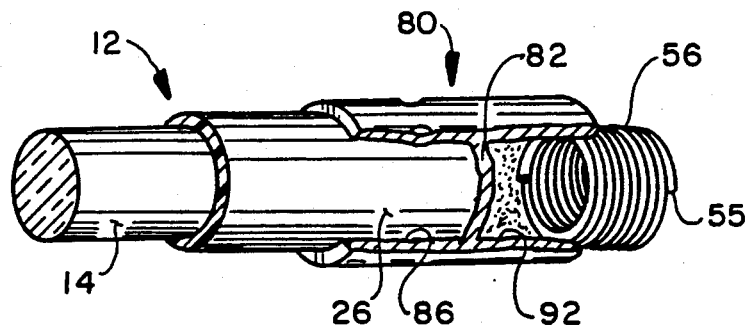
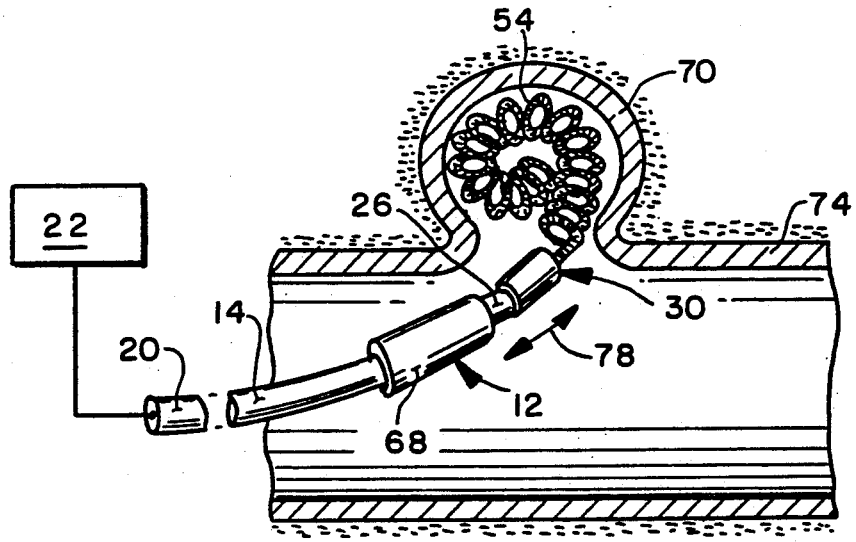

METHOD AND APPARATUS FOR PLACEMENT OF AN EMBOLIC COIL

BACKGROUND OF THE INVENTION

1. Field of the Invention

The present invention pertains to the endovascular treatment of aneurysms and the like, using embolic coils, and more particularly, pertains to the endovascular placement of such coils using introducer catheters.

2. Description of the Related Art

The endovascular treatment of a variety of lesions throughout the body has become an increasingly popular method of therapy. For example, introducer catheters have been used to place remedial devices and materials such as balloons, coils, particles, adhesive and alcohol to target lesions. One particular example is the treatment of an aneurysm by placing radiopaque materials within an aneurysm pouch. For example, it is known to push embolic coils through an introducer catheter, having a free end positioned at the desired deposition site. However, once the embolic coils leave the introducer catheter they are no longer under control and may become repositioned away from the desired location. This might occur, for example, when the treatment site is located near a vessel having a larger lumen, as when the embolic coil, having migrated to the larger vessel, would travel to a remote location.

Another example of coil placement is given in U.S. Pat. No. 4,512,338. The coils used are of shape memory alloy, becoming enlarged when warmed by the body within which they are placed. The coils are passed through an introducer catheter, the free end of which is located at the desired treatment site. The introducer catheter is preferably thermally insulated to prevent premature expansion of the treatment coil. When the coil is pushed mechanically past the free end of the catheter, it is exposed to the warmer bodily tissue and bodily fluids at the treatment site. Auxiliary heating sources, either relied upon as a sole source of heat, or used in conjunction with the body heat associated with the deposition site, could also be employed. For example, infrared radiation could be employed to progressively heat and reform the shape memory alloy wire.

Another example of intravascular catheter treatment is given in U.S. Pat. No. 4,735,201, and in a related article entitled "Laser-Induced Thermal Occlusion of Berry Aneurysms: Initial Experimental Results", by Gerald V. O'Riley, Patentee of U.S. Pat. No. 4,735,201, Mark D. Forrest, William C. Schoene and Richard H. Clarke, *Radiology*, 1989, Vol. 171, pp. 471-474. Disclosed is an intravascular laser-catheter technique for intracranial aneurysms, suitable for use at the time of diagnostic angiography. A fiber optic probe is inserted through an introducer catheter, the free end of which is located adjacent the treatment site. The catheter axis is located generally normal to the treatment site, for example, at the base of a vascular T-junction.

A metal cap having the configuration of a paraboloid, or the like rounded tip, is pushed through the introducer catheter by a fiber optic probe. A recess formed in the metal cap receives the free end of the fiber optic and hot melt adhesive is located in the recess to secure the metal cap to the free end of the optic fiber. The optic fiber is secured directly to the metal cap with hot melt adhesive.

The optic fiber is employed to push the metal cap through the introducer catheter into position with respect to the desired treatment site. A laser light source located at the proximal end of the optic fiber discharges laser energy through the optic fiber at two different levels. The optic fiber is advanced until the metal cap presses against the site to be repaired, and a relatively high level of laser radiation is transmitted through the optic fiber to heat the metal cap to the extent that it causes coagulation of the tissue surrounding the neck of the aneurysm. The metal cap is dimensioned larger than the neck of the aneurysm, with the optic fiber developing pressure against the metal cap during coagulation.

Heating of the metal cap to cause coagulation softens the hot melt glue, and if tension were applied to the optic fiber, the distal or free end thereof might become dislocated from the metal cap. After the metal cap is allowed to cool and a bond established with the tissue at the neck of the aneurysm, a second burst of laser energy is transmitted through the optic fiber, sufficient to soften the hot melt glue, and to facilitate withdrawal of the optic fiber end therefrom. The second laser burst, for removal of the optic fiber, is at a lower energy level than the burst for producing coagulation.

U.S. Pat. No. 4,795,458 teaches a stent made of shape memory alloy in either tape or wire form for vascular implantation to prevent restenosis after balloon angioplasty. The coil has a diameter less than that of the blood vessel in which it is to be implanted, and grows or swells when heated to maintain the blood vessel lumen. The coil is pushed through an introducer catheter to a repair site. Hot saline solution is then past through the catheter into the bore of the wire coil, heating the coil sufficient to cause a shape change (enlargement). However, as with the aforementioned coils, control over the coil is lost once the coil passes through the free end of the introducer catheter.

It is desirable in many applications to retain control over the coil position and to facilitate retraction of the coil during positioning, if necessary. U.S. Pat. No. 4,503,569 employs a coil of shape memory alloy which is transluminally positioned to serve as a prosthesis for an endovascular graft. A hot saline solution, passed through the introducer catheter, heats the coil to its transition temperature causing expansion of the coil. As with the coils previously mentioned, retraction is not possible as positioning of the coil is accomplished solely by pushing the coil through the introducer catheter. Thus, considerable care must be exercised to prevent over-extension of the catheter or probe during coil placement.

U.S. Pat. No. 3,868,956 discloses an expandable appliance such as coil of shape memory alloy, which is expandable when heated. The appliance is pushed through an introducer catheter. A pair of electrical conductors are attached to the expandable appliance and remain attached thereto when the appliance is delivered to the treatment site. A current is then passed through the electrical conductors to cause heating of the appliance. As the introducer catheter is withdrawn from the appliance, the electrical conductors are separated therefrom and are withdrawn from the body.

In addition to the techniques described above, directed to the endovascular or transluminal deposition of a repair appliance, various balloon embolization therapies have been developed. For example, a treatment is described in the article entitled "Giant Cavernous Aneurysm Associated With Trigeminal Artery: Treatment By Detachable Balloon", Higashida et al., *American*

*Journal of Neuroradiology*, 1981, Vol. 2, pp. 167-173. A related technique is reported in another article of the *American Journal of Neuroradiology*, entitled "Giant Unclippable Aneurysms: Treatment Detachable Balloons", by Debrun et al., Vol. 2., pp. 167-173, March/April 1981. These are examples of endovascular therapy of aneurysms, typically performed in patients with aneurysms that are surgically inaccessible. Two additional examples of balloon techniques are given in an article entitled "Intravascular Balloon Embolization of a Carotid-Opthalmic Artery Aneurysm With Preservation of the Parent Vessel", by Hieshima et al., *American Journal of Neuroradiology*, Vol. 7, pp. 916-918, September/October 1986; and an article by Higashida et al., "Cavernous Carotid Artery Aneurysm Associated With Marfan's Syndrome: Treatment By Balloon Embolization Therapy", *Neurosurgery* 1988, Vol. 22, No. 2, pp. 297-300. As an alternative to gas-filled balloons, U.S. Pat. No. 4,793,350 discloses a low profile dilatation catheter which eliminates the use of gas.

U.S. Pat. No. 4,425,908 discloses a blood clot filter of open wire, expandable configuration which is pushed through an introducer catheter and allowed to expand within a blood vessel. The expandable wire filter is passed through the catheter with a guide wire feeder device. U.S. Pat. No. 4,300,244 discloses a cardiovascular graft using a carbon-coated tightly wound spring to provide a biocompatible interior surface which provides an unobstructed passageway for blood flow. The arrangement provides a vascular prosthesis that can be readily installed in a relatively simple procedure.

Despite the above advances, several improvements are still being sought. For example, it is important in an endovascular procedure that the repair device be accurately positioned, to obtain maximum effectiveness. For example, in the treatment of aneurysms with embolic coils, it is important that the coils be accurately positioned with respect to the aneurysm pouch. At times, this requires not only extension, but also retraction of the embolic coil within the blood vessel.

SUMMARY OF THE INVENTION

It is an object according to the present invention to provide apparatus and methods for the endovascular placement of embolic coils and the like appliances, which permits repeated repositioning of the appliances.

It is another object according to the present invention to use commercially available embolic coils with the above apparatus and methods, thereby avoiding the expense and prolonged testing and approval of coils or other embolization devices of specialized design.

Yet another object according to the present invention is to provide a simple and accurate release mechanism for releasing the coil from a catheter probe.

Yet another object of the present invention is to provide a release mechanism for an embolic coil using heat releasable adhesive, and a laser energy source.

Yet another object of the present invention is to provide methods and apparatus for the endovascular placement of embolic coils for aneurysms of varying types and locations, and which does not require special techniques, such as maintaining a compression of the catheter probe against the repair device during endovascular placement.

These and other objects according to the present invention which will become apparent from studying the appended description and drawings, are provided in an apparatus for the embolization of a vascular aneurysm, comprising:

an optic fiber for transmitting light energy therethrough;

embolic coil means;

connector means for releasably mounting the embolic coil means, including a double-ended energy absorbing body of material which is heated when exposed to light energy, the body having means at one end for attachment to the optic fiber free end so as to remain attached thereto despite heating of the connector body, and means at the other end for slidably mounting the embolic coil means; and heat releasable adhesive means bonding the embolic coil means to the other end of the connector means.

Further objects are attained in a method for positioning an embolic coil at a treatment site to effect embolization of a vascular aneurysm, comprising the steps of:

providing an optic fiber for transmitting light energy therethrough;

providing a connector means for releasably mounting the embolic coil means, including a double-ended energy absorbing body of material which is heated when exposed to light energy;

crimpingly engaging the optic fiber with one end of the connector means, so as to assure attachment of the connector means to the fiber optic, despite heating of the connector body;

bringing the embolic coil means into contact with another end of the connector means;

bonding the embolic coil means to the other end of the connector means with a heat releasable adhesive means;

advancing the optic fiber toward the treatment site so as to position the embolic coil thereat;

transmitting light through the optic fiber to heat the connector means and to release the adhesive bond between the connector means and the embolic coil means; and moving the connector means out of engagement with the embolic coil means.

Additional objects according to the present invention are provided in an apparatus for the intravascular delivery of a therapeutic device, comprising:

an optic fiber for transmitting light energy therethrough connector means for releasably mounting the therapeutic device, including a double-ended energy absorbing body of material which is heated when exposed to light energy, the body having means at one end for attachment to the optic fiber free end so as to remain attached thereto despite heating of the connector body, and means at the other end for engaging the embolic coil means; and heat releasable adhesive means bonding the treatment device to the other end of the connector means.

Further objects according to the present invention are attained in a method for the intravascular positioning of a therapeutic device at a treatment site, comprising the steps of:

providing an optic fiber for transmitting light energy therethrough;

providing a connector means for releasably mounting the therapeutic device, including a double-ended energy absorbing body of material which is heated when exposed to light energy;

crimpingly engaging the optic fiber with one end of the connector means, so as to assure attachment of the connector means to the fiber optic, despite heating of the connector body;

contacting the therapeutic device on another end of the connector mean;

bonding the therapeutic device to the other end of the connector means with a heat releasable adhesive means;

advancing the optic fiber toward the treatment site so as to position the therapeutic device thereto;

transmitting light through the optic fiber to heat the connector means and to release the adhesive bond between the connector means and the therapeutic device; and moving the connector means out of engagement with the therapeutic device means.

BRIEF DESCRIPTION OF THE DRAWINGS

In the drawings, wherein like elements are referenced alike,

FIG. 1 is a fragmentary perspective view of an embolic coil being mounted on a placement apparatus according to principles of the present invention;

FIG. 2 is a perspective view of the embolic coil taken on an enlarged scale;

FIG. 3 is a cross-sectional view of the connector portion of FIG. 1;

FIG. 4 is a fragmentary perspective view showing an embolic coil being mounted to an alternative placement apparatus according to the present invention;

FIG. 5 is a cross-sectional view of the connector portion of FIG. 4;

FIG. 6 is a fragmentary cross-sectional view of an aneurysm being treated according to the principles of the present invention;

DETAILED DESCRIPTION OF THE PREFERRED EMBODIMENTS

Figure 7:
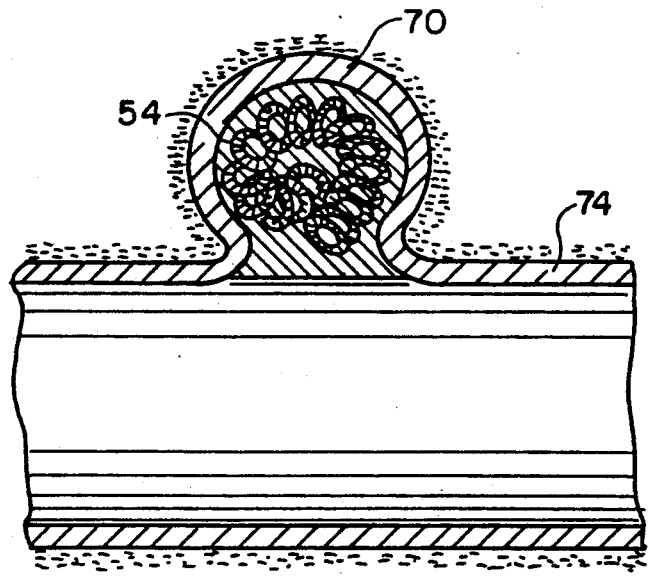
FIG. 7 is a cross-sectional view of the aneurysm after treatment.

Referring now to the drawings, and initially to FIG. 1, a placement apparatus for endovascular delivery of remedial appliances and especially for the embolization of aneurysms, is generally indicated at 10. The placement apparatus 10 includes a fiber-optic cable generally indicated at 12, comprising an optic fiber 14 encased in a sheath or cladding 16. The optic fiber 14 may be made of any suitable material such as quartz, and cladding 16 is preferably made of silica, but other biocompatible materials as are known in the art, may also be used.

Referring to FIG. 6, the distal end 20 of fiber-optic cable 12 is attached to an energy source 22 which transmits energetic light pulses through optic fiber 14 to its proximal end 26, located adjacent the treatment site. Referring to FIGS. 1 and 3, a connector device 30 is located at the proximal end 26 of fiber-optic cable 12 and cooperates to form a probe assembly therewith. The connector device 30 includes a body 32 of energy absorbing material which is heated when exposed to light energy.

Body 32 is preferably made of a suitable metal such as brass or a brass alloy, which is heated when exposed to laser light. The embolic coils used may or may not be radiopaque, and accordingly, it is important in some applications that the connector 30 be made of a material which is radiopaque so as to assist in guiding the embolic coil to the treatment site, and in detecting when the embolic coil is properly located within the aneurysm pouch.

Body 32 includes a cylindrical cable-mounting end 34 comprising a ferrule having an outer surface 46 and a cylindrical bore 36, the inner end of which is terminated at wall 38. In the preferred embodiment, the connector is made from the metallic distal tip of a TRIMEDYNE LASERPROBE—PLR PLUS catheter. The catheter is used for the ablation of atherosclerotic plaque and has a bulbous, generally ovoid tip adapted for that purpose. The tip was adapted for use in the present invention by grinding to assume the configurations illustrated in the figures.

The second coil-mounting end 40, which provides attachment for the embolic coil, has an outer surface 42 of reduced diameter, compared to the outer surface 46 of the first end 34. Thus, a step or shoulder 50 is located at one end of mounting portion 40. The proximal end 26 of fiber optic cable 12 is inserted into cable mounting portion 34 with the free end of optic fiber 14 preferably spaced a short distance from wall 38. The ferrule-like body of cable mounting portion 34 is thereafter swagged or crimped to engage cladding 16, thereby providing a light-tight seal, while securely retaining the connector device 30 on fiber-optic cable 12. This also provides a heat resistant retention which will remain intact, despite heating of connector body 32.

FIG. 2 illustrates a fully formed embolic coil 54 of conventional construction, such as that commercially available from the Cook Company of Bloomington, Ind., Catalog Number MWCE-38-5-8. However, coil 54 may be of virtually any type known in the art to be suitable for the embolization of vascular aneurysms. The embolic coil is preferably made of wound wire 55, but may also be made of monolithic wire or of a polymer composition, for example. The wound wire of coil 54 has a mounting end 56 which is recessed to form a socket. The outer diameter of coil-mounting portion 40 is dimensioned approximately equal to or slightly smaller than the central bore of the mounting socket 56 of embolic coil 54. The mounting end 56 of coil 54 is telescopically inserted over the free end of coil mounting portion 40, being advanced in the direction of arrow 60, as illustrated in FIG. 1. To facilitate mounting of coil 54, the aforementioned shoulder 50 is provided to limit the telescopic insertion of the coil on coil mounting end 56 on coil mounting portion 40. The wound wire 55 of embolic coil 54 and the coil-mounting portion 40 of connector 30 are preferably dimensioned such that the coil mounting end 56, slides freely about coil mounting portion 40.

According to an important feature of the present invention, the coil 54 is readily detachable, on demand, from coil mounting portion 40. Light energy, preferably in the form of laser light is transmitted by source 22 along optic fiber 14. The laser light emanates from the proximal end 26 of optic fiber 14, that end portion received within cable mounting portion 34, and terminated immediately adjacent interior wall 38 of body 32. Laser light leaving optic fiber 14 irradiates wall 38 and is trapped within the crimped cylindrical body of cable mounting portion 34. Laser energy is efficiently converted into heat, which warms body 32 and, importantly, the coil-mounting portion 40, thereof.

As will be appreciated by those skilled in the art, the wound wire of coil 54 itself comprises a continuous helical coil having a small radius hollow bore, of size on the order of the wire diameter (0.038 inches in the preferred embodiment). The coil may be obtained commercially, and as such may be found to be filled with fibrous material such as DACRON used in applications outside the invention to promote clotting. As will be seen, the present invention contemplates retraction of the coiled wound wire into the introducer catheter which delivered it to the treatment site. It is therefore desirable to remove as much of the fibrous material as possible from the wound wire outer surface, to allow retraction back into the catheter. The fibrous material presents no problem in conventional applications because when the coil is pushed out of the catheter, it is separated from the catheter apparatus, and no retraction of the coil is possible, or even contemplated.

According to one aspect of the present invention, a heat releasable adhesive is applied to the outer surface 42 of coil-mounting portion 40, or to the inner bore 56 of embolic coil 54, or both, to form a bond which retains coil 54 on connector device 30. According to another important aspect of the present invention, the heat releasable adhesive 64 bonding the coil mounting end to connector 30 has a release temperature considerably higher than temperatures which may be encountered in a body cavity or blood stream.

The adhesive 64 is preferably of a hot melt type, commercially available from the BOSTIK Company of Middleton, Mass., being sold as Catalog No. 6383. Other suitable heat sensitive adhesives may also be used and it is preferred that such adhesives have a softening or release temperature between 100° F., and 250° F. The hot melt adhesive described above has a softening range of 75° C. to 92° C. The adhesive is applied to the coil mounting end of connector 30, and the coil mounting end is inserted thereover, the assembly thereafter being set aside until the bond strength of the adhesive is developed.

Thereafter, the coil is straightened if it has been removed from its delivery tube and the probe assembly is inserted into a conventional introducer catheter 68. The catheter preferably comprises an introducer catheter sold by the Cook Company of Bloomington, Ind., as Catalog Item No. HHS-1. Preferably, the connector 30 and embolic coil 54 mounted thereon are carried within the catheter, as the catheter tip is located at the treatment site, in the manner illustrated in FIG. 6. Thereafter, the fiber-optic cable is extended beyond the free end of the catheter, toward the aneurysm pouch 70.

As will be appreciated by those skilled in the art, the present invention offers a significant advantage in allowing the connector and embolic coil bonded thereto to be moved back and forth in the directions of double-headed arrow 78. The embolic coils may be extended and retracted as many times as may be desired until an optimum positioning thereof is achieved. It is important that the embolic coils be located entirely within the aneurysm pouch, and do not extend into the vessel 74. Further, it is important that the embolic coils be securely retained in the aneurysm pouch, and not be allowed to travel through the vessel.

The bond between the coil and the connector is reliable and easily withstands the tension forces during retraction of the coiled spring, when the spring is unwound or straightened as the trailing end thereof is drawn toward the proximal end of the catheter. As those skilled in the art will appreciate, a considerable coiling force may be built into the embolic coils, and this force must be overcome if the embolic device is to be uncoiled. In some instances, the embolic coil may have a substantial angular displacement from the longitudinal axis of the catheter distal end portion, thus contributing to the retraction force, especially when the embolic device is made from a wound wire construction, where each winding must cam over the distal end of the catheter. Retraction forces must be further increased for certain non-circular embolic coil configurations. For example, the coil may have generally triangular windings with rounded corners. The present invention has been found to reliably retract these coil configurations innumerable times. It is important, however, that conventional extend-only embolic coils filled with DACRON or other fibrous material be modified eliminating most if not all of the exposed fibers, to eliminate clotting during a placement procedure.

After the coil is positioned at a desired location, a laser pulse is transmitted by source 22 through optic fiber 14, so as to be incident on connector 30, and especially the wall 38 thereof, thereby heating the connector body. Heat is conducted through the coil mounting portion 40, to the outer surface 42 thereof, thereby softening or otherwise releasing the heat releasable adhesive bonding the embolic coil to the coil-mounting portion. With frictional engagement of the embolic coil to the aneurysm pouch, or to tissue or the like located therein, the probe assembly and the coil-mounting portion thereof is readily withdrawn from the inner bore of the embolic coil, thereby leaving the embolic coil in its desired position.

It has been found that the present invention provides a quick and easy release of the embolic coil, without disturbing its desired position. After placement of the coil, the catheter and optic fiber with connector 30 attached, are withdrawn from the vessel, leaving the aneurysm pouch filled with the embolic appliance. For example, FIG. 7 shows an aneurysm pouch 70 filled with an embolic coil 54. In time, tissue is formed about the coils, filling the aneurysm pouch and effecting a repair of the aneurysm site.

Turning now to FIGS. 4 and 5, an alternative embodiment of the present invention includes a connector generally indicated at 80 connected to the proximal end 26 of fiber-optic cable 12. The connector 80 includes a body 82 formed of a material such as brass or brass alloy or other suitable materials, which are heated when exposed to light, and especially to laser energy. Connector body 82 includes a cable-mounting portion 84 comprising a ferrule having an internal bore 86 terminating in an inner end wall 88. As with the connector 30 of FIG. 3, the proximal end of fiber-optic cable 26 is inserted in the inner bore 86 and the ferrule-like body is swagged or crimped thereabout, to form a substantially light-tight connection with the fiber-optic cable which is secure, even when the connector 80 is heated.

A coil-mounting portion 90 is located at the other end of connector 80 and includes a socket with an internal bore 92 for receiving a helical embolic coil, such as the coil 54 illustrated in FIG. 2. The outer surface of coil 54, or the internal bore 92 of the coil-mounting portion 90 or both are treated with a heat releasable adhesive, such as the adhesive 64 described above. A sleeve of hot melt adhesive may be inserted between the coil mounting end and the coil mounting portion 90, and the connector portion 90 can be heated by suitable means to activate the adhesive. Thus, the embolic coil is securely mounted to the connector once the adhesive achieves the desired bond strength.

The laser pulse transmitted through optic fiber 14 heats connector body 82, softening or otherwise releasing the adhesive bonding the outer surface of the embolic coil to the inner bore 92. At this point, the optic fiber can be withdrawn away from the embolic coil, with a telescopic motion. It is preferred that the walls of internal bore 92 be smooth, so that the embolic coil can be quickly and easily separated from the connector, allowing the connector, fiber-optic cable and catheter to be withdrawn from the treatment site.

Figure 8:
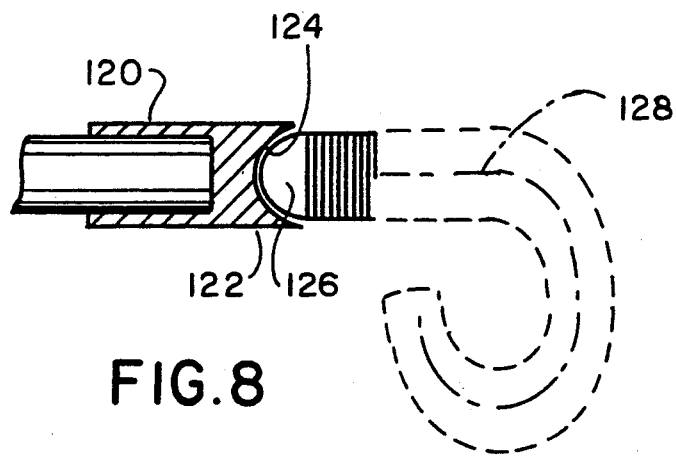
FIGS. 8 and 9 show alternative embodiments of a coil-mounting connector.

FIG. 8 shows an alternative connector embodiment, where the coil mounting end 122 of the connector 120 has a concave recess 124. The mounting end 126 of coil 128 has a convex tip receivable in the recess, and secured thereto with a heat sensitive adhesive such as the hot melt adhesive described above. It may be desirable to increase the curvature of the recess, compared to the coil tip, to form a cavity between the connector and coil tip to ensure the adhesive is not forced out during assembly.

Figure 9:
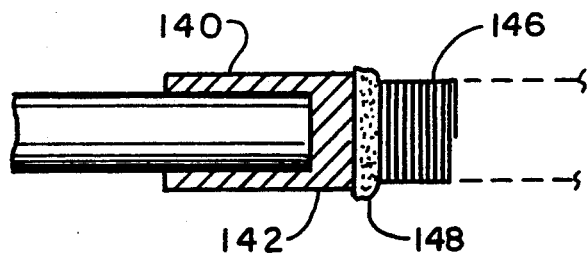

In each of the above examples, the coil mating surfaces of the coil mounting portion of the connector extend in a longitudinal direction, to apply the tension forces of retraction as a shear stress loading on the adhesive. While this is the preferred arrangement, other arrangements are also possible. For example, the coil mounting end of the connector can be terminated at a blunt surface. For example, the connector 140 of FIG. 9 is truncated to form a coil mounting portion 142 with a circular end face. The coil end 146 is butted against the circular face and secured thereto with heat releasable adhesive 148.

As can be seen from the above, the present invention allows repositioning of embolic coils, such that the coils are deposited within an aneurysm pouch, and the coil can be repositioned innumerable times until the preferred location is attained. Thus, careful control over positioning of the coils can be achieved to insure that the coils are located entirely within the aneurysms pouch, without extension of the coil into the native vessel. Laser activation disassociates the bond between the coil and the probe assembly.

Although embolic coils have been described in the preferred embodiment, it will now be appreciated that therapeutic devices having a variety of shapes, such as radioactive therapeutic capsules can be quickly and accurately positioned using the present invention.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. Apparatus for the embolization of a vascular aneurysm, comprising:
   an optic fiber for transmitting light energy therethrough, having a free end and an other end;
   embolic coil means;
   connector means for releasably mounting the embolic coil means, including a double-ended energy absorbing body of material which absorbs heat when exposed to light energy, the body having means at one end for attachment to the optic fiber free end so as to remain attached thereto despite heating of the connector body, and means at the other end for engaging the embolic coil means; and
   heat releasable adhesive means bonding the embolic coil means to the other end of the connector means.

2. The apparatus of claim 1 wherein the one end of the connector means body comprises a ferrule crimped to the optic fiber free end.

3. The apparatus of claim 1 wherein the embolic coil has an internal bore and the other end of the connector means body is dimensioned to be received in the internal body of the embolic coil.

4. The apparatus of claim 1 wherein the other end of the connector means body defines an internal recess and the embolic coil has an end dimensioned to be received in the internal recess of the connector means body.

5. The apparatus of claim 1 wherein the embolic coil has an outer surface and the other end of the connector means body defines an internal bore dimensioned to receive the embolic coil.

6. A method for positioning an embolic coil at a treatment site to effect embolization of a vascular aneurysm, comprising the steps of:
   providing an optic fiber for transmitting light energy therethrough;
   providing a connector means for releasably mounting the embolic coil means, including a double-ended energy absorbing body of material which is heated when exposed to light energy;
   crimpingly engaging the optic fiber with one end of the connector means, so as to assure attachment of the connector means to the fiber optic, despite heating of the connector body;
   bringing the embolic coil means into contact with another end of the connector means;
   bonding the embolic coil means to the other end of the connector means with a heat releasable adhesive means;
   advancing the optic fiber toward the treatment site so as to position the embolic coil thereat;
   transmitting light through the optic fiber to heat the connector means and to release the adhesive bond between the connector means and the embolic coil means; and
   moving the connector means out of engagement with the embolic coil means.

7. Apparatus for the intravascular delivery of a therapeutic device, comprising:
   an optic fiber for transmitting light energy therethrough, having a free end and an other end;
   connector means for releasably mounting the therapeutic device, including a double-ended energy absorbing body of material which is heated when exposed to light energy, the body having means at one end for attachment to the optic fiber free end so as to remain attached thereto despite heating of the connector body, and means at the other end for engaging the therapeutic device; and
   heat releasable adhesive means for bonding the therapeutic device to the other end of the connector means.

8. The apparatus of claim 7 wherein the one end of the connector means body comprises a ferrule crimped to the optic fiber free end.

9. The apparatus of claim 7 wherein the other end of the connector means body has an outer surface for butt engagement with the therapeutic device.

10. The apparatus of claim 7 wherein the other end of the connector means body defines an internal bore adapted to receive an outer surface of the therapeutic device so as to overlie said outer surface of the therapeutic device.

11. A method for the intravascular positioning of a therapeutic device at a treatment site, comprising the steps of:

providing an optic fiber for transmitting light energy therethrough;

providing a connector means for releasably mounting the therapeutic device, including a double-ended energy absorbing body of material which is heated when exposed to light energy;

crimpingly engaging the optic fiber with one end of the connector means, so as to assure attachment of the connector means to the fiber optic, despite heating of the connector body;

contacting the therapeutic device on another end of the connector means; and bonding the therapeutic device to the other end of the connector means with a heat releasable adhesive means;

advancing the optic fiber toward the treatment site so as to position the therapeutic device thereat;

transmitting light through the optic fiber to heat the connector means and to release the adhesive bond between the connector means and the therapeutic device; and moving the connector means out of engagement with the therapeutic device means.

12. The method of claim 11 wherein the therapeutic device defines a recess and the step of contacting the therapeutic device with another end of the connector means comprises the step of inserting the other end of the connector in the therapeutic device recess.

13. The method of claim 11 wherein the other end of the connector means defines a recess and the step of contacting the therapeutic device with another end of the connector means comprises the step of inserting the therapeutic device into the connector means recess.

* * * * *

UNITED STATES PATENT AND TRADEMARK OFFICE
CERTIFICATE OF CORRECTION

PATENT NO. : 5,108,407

DATED : April 28, 1992

INVENTOR(S) : Glen K. Geremia, et al.

It is certified that error appears in the above-identified patent and that said Letters Patent is hereby corrected as shown below:

On the title page, Item [56]:

On the Face of the Patent, under the heading "References Cited - U.S. Patent Documents", change the name "Millstead" to read --Hillstead--.

In Column 3, line 4, after the word "Treatment" insert the word --With--.

In Column 10, line 12, (Claim 3) change the word "body" to read --bore--.

Signed and Sealed this

Tenth Day of August, 1993

Attest:

MICHAEL K. KIRK

Attesting Officer

Acting Commissioner of Patents and Trademarks